United States Patent
Olson

(10) Patent No.: US 6,554,816 B1
(45) Date of Patent: Apr. 29, 2003

(54) ABSORBENT ARTICLES WITH SHAPED FASTENING COMPONENT

(75) Inventor: Christopher Peter Olson, Neenah, WI (US)

(73) Assignee: Kimberly-Clarke Worldwide, Inc., Neenah, WI (US)

( * ) Notice: Subject to any disclaimer, the term of this patent is extended or adjusted under 35 U.S.C. 154(b) by 0 days.

(21) Appl. No.: 09/444,633

(22) Filed: Nov. 22, 1999

(51) Int. Cl.⁷ .................................................. A61F 13/15
(52) U.S. Cl. ....................................... 604/386; 604/391
(58) Field of Search ....................... 604/385.01, 385.21, 604/385.23, 385.24, 385.25, 385.28, 385.3, 386, 387, 391, 389, 390

(56) References Cited

U.S. PATENT DOCUMENTS

| | | |
|---|---|---|
| 2,957,512 A | 10/1960 | Wade et al. |
| 3,039,466 A | 6/1962 | Wilson |
| 3,277,547 A | 10/1966 | Billarant |
| 3,316,139 A | 4/1967 | Alford et al. |
| 3,319,307 A | 5/1967 | Marforio |
| 3,577,607 A | 5/1971 | Ikoma et al. |
| 3,694,867 A | 10/1972 | Stumpf |
| 3,842,832 A | 10/1974 | Wideman et al. |
| 3,842,837 A | 10/1974 | Sward |
| 3,943,981 A | 3/1976 | De Brabander |
| 4,051,854 A | 10/1977 | Aaron |
| 4,122,552 A | 10/1978 | Tedford |
| 4,145,763 A | 3/1979 | Abrams et al. |
| 4,201,203 A | 5/1980 | Applegate |
| 4,205,679 A | 6/1980 | Repke et al. |

(List continued on next page.)

FOREIGN PATENT DOCUMENTS

| | | |
|---|---|---|
| CA | 2096672 | 11/1997 |
| DE | 35 33 881 A1 | 4/1986 |
| DE | 196 54 052 C1 | 12/1997 |
| DE | 197 27 916 A1 | 6/1998 |
| EP | 0 320 991 A2 | 6/1989 |
| EP | 0 217 032 B1 | 2/1992 |
| EP | 0 520 087 A1 | 12/1992 |
| EP | 0 526 868 A2 | 2/1993 |
| EP | 0 321 232 B1 | 5/1993 |
| EP | 0 476 992 B1 | 7/1995 |
| EP | 0 487 921 B1 | 9/1995 |
| EP | 0 433 951 B1 | 8/1996 |
| EP | 0 696 911 B1 | 1/1997 |
| EP | 0 756 855 A1 | 2/1997 |
| EP | 0 570 980 B1 | 7/1997 |
| EP | 0 812 584 A2 | 12/1997 |
| EP | 0 878 180 A2 | 11/1998 |
| EP | 0 757 550 B1 | 12/1998 |
| EP | 0 945 110 A2 | 9/1999 |
| EP | 0 641 552 B1 | 12/1999 |

(List continued on next page.)

OTHER PUBLICATIONS

Advertisement from *One Step Ahead*®catalog, Late Winter 2000, cover pages and page 26 referencing "Handy's Training Pants," and a photocopy of a package of Handy's Junior Training Pants as advertised therein.

Primary Examiner—Aaron J. Lewis
Assistant Examiner—Jamisue A. Webb
(74) Attorney, Agent, or Firm—Thomas H. Gage; M. Michael Kubicki

(57) ABSTRACT

A disposable absorbent article includes a fastening system that can be repeatedly fastened, unfastened and refastened. The fastening components have interior corners near the leg openings and disposed toward the longitudinal and transverse center of the absorbent article that are recessed to avoid possible irritation of the wearer's skin.

20 Claims, 6 Drawing Sheets

U.S. PATENT DOCUMENTS

| | | |
|---|---|---|
| 4,209,563 A | 6/1980 | Sisson |
| 4,244,368 A | 1/1981 | Caradonna |
| 4,253,461 A | 3/1981 | Strickland et al. |
| 4,259,957 A | 4/1981 | Sonenstein et al. |
| 4,338,938 A | 7/1982 | Seavitt |
| 4,402,690 A | 9/1983 | Redfern |
| 4,418,123 A | 11/1983 | Bunnelle et al. |
| 4,446,189 A | 5/1984 | Romanek |
| 4,496,360 A | 1/1985 | Joffe et al. |
| 4,516,975 A | 5/1985 | Mitchell |
| 4,560,381 A | 12/1985 | Southwell |
| 4,581,772 A | 4/1986 | Smith |
| 4,585,447 A | 4/1986 | Karami |
| 4,610,680 A | 9/1986 | LaFleur |
| 4,610,682 A | 9/1986 | Kopp |
| 4,615,695 A | 10/1986 | Cooper |
| 4,619,649 A | 10/1986 | Roberts |
| 4,623,339 A | 11/1986 | Ciraldo et al. |
| 4,650,483 A | 3/1987 | Joffe |
| 4,655,760 A | 4/1987 | Morman et al. |
| 4,657,802 A | 4/1987 | Morman |
| 4,662,875 A | 5/1987 | Hirotsu et al. |
| 4,663,220 A | 5/1987 | Wisneski et al. |
| 4,699,622 A | 10/1987 | Toussant et al. |
| 4,701,170 A | 10/1987 | Wilson et al. |
| 4,701,176 A | 10/1987 | Wilson et al. |
| 4,704,116 A | 11/1987 | Enloe |
| 4,705,710 A | 11/1987 | Matsuda |
| 4,714,096 A | 12/1987 | Guay |
| 4,718,901 A | 1/1988 | Singheimer |
| 4,720,415 A | 1/1988 | Wielen et al. |
| 4,725,473 A | 2/1988 | Van Gompel et al. |
| 4,743,239 A | 5/1988 | Cole |
| 4,756,709 A | 7/1988 | Stevens |
| 4,761,318 A | 8/1988 | Ott et al. |
| 4,770,656 A | 9/1988 | Proxmire et al. |
| 4,771,483 A | 9/1988 | Hooreman et al. |
| 4,789,699 A | 12/1988 | Kieffer et al. |
| 4,834,742 A | 5/1989 | Wilson et al. |
| 4,847,134 A | 7/1989 | Fahrenkrug et al. |
| 4,850,988 A | 7/1989 | Aledo et al. |
| 4,850,992 A | 7/1989 | Amaral et al. |
| 4,863,785 A | 9/1989 | Berman et al. |
| 4,894,060 A | 1/1990 | Nestegard |
| 4,895,569 A | 1/1990 | Wilson et al. |
| 4,923,456 A | 5/1990 | Proxmire |
| 4,936,840 A | 6/1990 | Proxmire |
| 4,938,757 A | 7/1990 | Van Gompel et al. |
| 4,940,464 A | 7/1990 | Van Gompel et al. |
| 4,963,140 A | 10/1990 | Robertson et al. |
| 5,019,073 A | 5/1991 | Roessler et al. |
| 5,032,122 A | 7/1991 | Noel et al. |
| 5,046,272 A | 9/1991 | Vogt et al. |
| 5,062,839 A | 11/1991 | Anderson |
| 5,087,253 A * | 2/1992 | Cooper .................... 604/385.1 |
| 5,104,116 A | 4/1992 | Pohjola |
| 5,114,781 A | 5/1992 | Morman |
| 5,116,662 A | 5/1992 | Morman |
| 5,151,092 A | 9/1992 | Buell et al. |
| 5,176,671 A | 1/1993 | Roessler et al. |
| 5,185,052 A | 2/1993 | Chappell et al. |
| 5,224,405 A | 7/1993 | Pohjola |
| 5,226,992 A | 7/1993 | Morman |
| 5,242,436 A | 9/1993 | Weil et al. |
| 5,256,231 A | 10/1993 | Gorman et al. |
| 5,315,716 A | 5/1994 | Baum |
| 5,318,555 A | 6/1994 | Siebers et al. |
| 5,326,612 A | 7/1994 | Goulait |
| 5,342,341 A | 8/1994 | Igaue et al. |
| 5,370,634 A | 12/1994 | Ando et al. |
| 5,380,313 A | 1/1995 | Goulait et al. |
| 5,383,872 A | 1/1995 | Roessler et al. |
| 5,385,775 A | 1/1995 | Wright |
| 5,399,219 A | 3/1995 | Roessler et al. |
| 5,401,275 A | 3/1995 | Flug et al. |
| 5,407,439 A | 4/1995 | Goulait |
| 5,413,654 A | 5/1995 | Igaue et al. |
| 5,451,219 A | 9/1995 | Suzuki et al. |
| 5,476,702 A | 12/1995 | Datta et al. |
| 5,496,298 A | 3/1996 | Kuepper et al. |
| 5,503,908 A | 4/1996 | Faass |
| 5,527,602 A * | 6/1996 | Endres et al. ............ 604/385.1 |
| 5,531,731 A | 7/1996 | Brusky |
| 5,531,732 A | 7/1996 | Wood |
| 5,542,942 A | 8/1996 | Kline et al. |
| 5,546,608 A | 8/1996 | Russano |
| 5,547,531 A | 8/1996 | Allen et al. |
| 5,549,591 A | 8/1996 | Landvogt |
| 5,554,239 A | 9/1996 | Datta et al. |
| 5,569,233 A | 10/1996 | Goulait |
| 5,591,155 A | 1/1997 | Nishikawa et al. |
| 5,595,567 A | 1/1997 | King et al. |
| 5,603,708 A | 2/1997 | Seth |
| 5,605,735 A | 2/1997 | Zehner et al. |
| 5,606,781 A | 3/1997 | Provost et al. |
| 5,611,791 A | 3/1997 | Gorman et al. |
| 5,615,460 A | 4/1997 | Weirich et al. |
| 5,616,394 A | 4/1997 | Gorman et al. |
| 5,620,432 A | 4/1997 | Goulait et al. |
| 5,624,427 A | 4/1997 | Bergman et al. |
| 5,624,429 A | 4/1997 | Long et al. |
| 5,643,397 A | 7/1997 | Gorman et al. |
| 5,647,864 A | 7/1997 | Allen et al. |
| H1674 H | 8/1997 | Ames et al. |
| 5,655,843 A | 8/1997 | Conrad et al. |
| 5,669,897 A | 9/1997 | Lavon et al. |
| 5,669,900 A | 9/1997 | Bullwinkel et al. |
| 5,681,302 A | 10/1997 | Melbye et al. |
| 5,685,873 A * | 11/1997 | Bruemmer .................. 604/373 |
| 5,722,969 A | 3/1998 | Ito et al. |
| 5,735,840 A | 4/1998 | Kline et al. |
| 5,749,866 A | 5/1998 | Roe et al. |
| 5,759,181 A | 6/1998 | Sayama et al. |
| 5,766,389 A | 6/1998 | Brandon et al. |
| 5,779,831 A | 7/1998 | Schmitz |
| 5,782,819 A | 7/1998 | Tanzer et al. |
| 5,785,699 A | 7/1998 | Schmitz |
| 5,795,350 A | 8/1998 | Schmitz |
| 5,814,178 A | 9/1998 | Jacobs |
| 5,830,206 A | 11/1998 | Larsson |
| 5,830,298 A | 11/1998 | Jackson |
| 5,843,068 A | 12/1998 | Allen et al. |
| 5,846,262 A | 12/1998 | Sayama et al. |
| 5,851,205 A | 12/1998 | Hisada et al. |
| 5,853,405 A | 12/1998 | Suprise |
| 5,855,574 A | 1/1999 | Kling et al. |
| 5,879,500 A | 3/1999 | Herrin et al. |
| 5,888,607 A | 3/1999 | Seth et al. |
| 5,891,122 A | 4/1999 | Coates |
| 5,891,547 A | 4/1999 | Lawless |
| 5,897,545 A | 4/1999 | Kline et al. |
| 5,897,546 A | 4/1999 | Kido et al. |
| 5,897,547 A | 4/1999 | Schmitz |
| 5,899,895 A | 5/1999 | Robles et al. |
| 5,906,008 A | 5/1999 | Heki et al. |
| 5,911,713 A | 6/1999 | Yamada et al. |
| 5,921,977 A | 7/1999 | Schmitz |
| 5,925,027 A | 7/1999 | Schmitz |
| 5,926,926 A | 7/1999 | Kato |
| 5,928,212 A | 7/1999 | Kline et al. |
| 5,957,908 A | 9/1999 | Kline et al. |

| | | | | | | |
|---|---|---|---|---|---|---|
| 5,967,665 A | 10/1999 | MacDonald et al. | JP | 6-30962 A | 2/1994 |
| 5,968,031 A | 10/1999 | Schmitz | JP | 6-55623 U | 8/1994 |
| 5,997,521 A | 12/1999 | Robles et al. | JP | 6-285113 A | 10/1994 |
| 5,997,981 A | 12/1999 | McCormack et al. | JP | 7-116191 A | 5/1995 |
| 6,022,430 A | 2/2000 | Blenke et al. | JP | 9-66071 A | 3/1997 |
| 6,027,485 A | 2/2000 | Matsushita et al. | JP | 9-187477 A | 7/1997 |
| 6,030,373 A | 2/2000 | VanGompel et al. | JP | 11-99178 A | 4/1999 |
| 6,063,466 A | 5/2000 | Tuschy et al. | WO | WO 93/17648 A1 | 9/1993 |
| 6,086,571 A | 7/2000 | Guevara et al. | WO | WO 95/02383 A1 | 1/1995 |
| 6,099,516 A | 8/2000 | Pozniak et al. | WO | WO 95/18589 A1 | 7/1995 |
| 6,113,717 A | 9/2000 | Vogt et al. | WO | WO 95/27460 A1 | 10/1995 |
| 6,146,738 A | 11/2000 | Tsuji et al. | WO | WO 95/27461 A1 | 10/1995 |
| D437,932 S | 2/2001 | Ruman et al. | WO | WO 95/27462 A1 | 10/1995 |
| D437,933 S | 2/2001 | Fletcher et al. | WO | WO 95/27463 A1 | 10/1995 |
| D438,614 S | 3/2001 | Ratliff et al. | WO | WO 95/29657 A1 | 11/1995 |
| D439,662 S | 3/2001 | Ratliff et al. | WO | WO 96/19960 A1 | 7/1996 |
| 6,210,388 B1 | 4/2001 | Widlund et al. | WO | WO 96/41604 A1 | 12/1996 |
| 6,213,991 B1 | 4/2001 | Kling et al. | WO | WO 97/04729 A1 | 2/1997 |
| 6,230,374 B1 | 5/2001 | Widlund | WO | WO 97/23180 A1 | 7/1997 |
| 6,264,643 B1 | 7/2001 | Toyoda | WO | WO 97/36566 A1 | 10/1997 |
| 6,287,287 B1 | 9/2001 | Elsberg | WO | WO 97/46197 A1 | 12/1997 |
| 6,302,871 B1 | 10/2001 | Nakao et al. | WO | WO 97/48359 A1 | 12/1997 |
| 6,328,725 B2 | 12/2001 | Fernfors | WO | WO 98/18421 A1 | 5/1998 |
| 6,329,016 B1 | 12/2001 | Shepard et al. | WO | WO 98/18422 A1 | 5/1998 |
| 6,332,250 B1 | 12/2001 | Igaue et al. | WO | WO 99/53881 A1 | 10/1999 |
| 6,352,528 B1 | 3/2002 | Weber et al. | WO | WO 99/65441 A1 | 12/1999 |
| 6,447,497 B1 | 9/2002 | Olson | WO | WO 00/15069 A1 | 3/2000 |
| 6,454,751 B1 | 9/2002 | Olson | WO | WO 00/19950 A1 | 4/2000 |
| 2002/0095131 A1 | 7/2002 | Olson | WO | WO 00/19951 A1 | 4/2000 |
| 2002/0099353 A1 | 7/2002 | Olson | WO | WO 00/20206 A1 | 4/2000 |
| | | | WO | WO 00/20207 A1 | 4/2000 |

FOREIGN PATENT DOCUMENTS

| | | | | | |
|---|---|---|---|---|---|
| EP | 0 755 239 B1 | 12/1999 | WO | WO 00/23025 A1 | 4/2000 |
| EP | 0 800 379 B1 | 12/1999 | WO | WO 00/27236 A1 | 5/2000 |
| EP | 0 719 534 B1 | 4/2000 | WO | WO 00/27328 A1 | 5/2000 |
| EP | 0 721 769 B1 | 5/2000 | WO | WO 00/27329 A1 | 5/2000 |
| EP | 0 721 770 B1 | 5/2000 | WO | WO 00/30581 A1 | 6/2000 |
| EP | 0 547 497 B2 | 7/2000 | WO | WO 00/30584 A1 | 6/2000 |
| EP | 0 765 148 B1 | 11/2000 | WO | WO 00/35395 A2 | 6/2000 |
| FR | 1375254 | 9/1963 | WO | WO 00/35398 A1 | 6/2000 |
| GB | 1 520 740 | 8/1978 | WO | WO 00/37009 A2 | 6/2000 |
| GB | 2 267 024 A | 11/1993 | WO | WO 00/37016 A1 | 6/2000 |
| GB | 2 303 045 A | 2/1997 | WO | WO 00/74621 A1 | 12/2000 |
| GB | 2 315 402 A | 2/1998 | WO | WO 01/88245 A2 | 11/2001 |
| JP | 5-84322 U | 11/1993 | | | |

* cited by examiner

ABSORBENT ARTICLES WITH SHAPED FASTENING COMPONENT

BACKGROUND OF THE INVENTION

The present invention relates to absorbent articles which are adapted to contain body exudates. More particularly, the invention pertains to pant-like disposable absorbent articles having non-irritating refastenable seams, and methods of making such disposable absorbent articles.

Current disposable absorbent training pants for children going through the potty training stage have proved to be a particularly desirable and useful product. Such training pants generally include an absorbent chassis including a liquid impervious outer cover, a liquid pervious bodyside liner and an absorbent structure. The training pants further include stretchable side panels that are permanently bonded to opposite side edges of the absorbent chassis. The chassis and side panels thereby form a unitary waist opening and two leg openings. The fit of the pants may be further enhanced by gathering means along the waist and leg openings.

The components of traditional training pants are permanently seamed together to provide a pant product. Thus, traditional training pants do not employ fastening components such as hook-and-loop type fasteners which can irritate the skin if the fastening components come in contact with the wearer. Moreover, traditional training pants are useful in the toilet training process because the pant has a very garment-like look. Children identify diaper products with babies, and most children do not like being identified with or as babies. Consequently, these children do not want to wear baby diapers, and instead prefer to wear training pants that look like adult underwear. Thus, the switch from a traditional diaper to a more garment-like or underwear-like training pant can be an important step in the toilet training process.

One drawback with current training pants, however, is that the manner of applying them is limited to being pulled on like a pant. Applying the product like a pant is advantageous in many instances, and is particularly suited for active, walking children. Even for the same child, however, there may be times when it would be useful to apply the product like a diaper. For instance, it might be more convenient to apply the product like a diaper when there is a desire not to remove the child's shoes. Because it is difficult to know when a particular mode of applying the garment will be needed, it is beneficial to have a garment that is adaptable to being used either as a diaper or as a pant. This is preferable to keeping both types of garments available. A product that can be applied either like a diaper or a pant permits the interior of the product to be easily checked without having to pull the product downward.

Thus, it would be desirable to have a disposable absorbent article that provides the garment-like look of a traditional training pant, includes fastening components to allow application either like a diaper or a pant, and minimizes the likelihood of fastening components coming into contact with the skin of the wearer.

SUMMARY OF THE INVENTION

In response to the above-referenced unfulfilled need in the art, a new pant-like disposable absorbent article with shaped fastening components and a method of making such a disposable absorbent article have been discovered. The absorbent article includes a fastening system that can be repeatedly fastened, unfastened and refastened. The fastening components have interior corners near the leg openings that are recessed to avoid possible irritation of the wearer's skin.

In one embodiment, the present invention pertains to an absorbent article including an absorbent chassis and a fastening system. The absorbent chassis defines a longitudinal axis, a transverse axis, opposite first and second waist regions, and a crotch region which extends between and interconnects the first and second waist regions. The fastening system includes first and second fastening components disposed in the first waist region and adapted to releasably engage at least one mating fastening component disposed in the second waist region. Each first and second fastening component defines an interior corner disposed toward the longitudinal and transverse center of the absorbent chassis, and the interior corner is recessed.

The fastening components and the mating fastening components form refastenable seams for securing the first and second waist regions together. The refastenable seams allow the product to be either pulled on like a pant or applied like a diaper. If the training pant becomes soiled during use, the fastening components can be disengaged from the mating fastening components to easily remove the training pant from the waist of the wearer with reduced risk of undesirably soiling the clothes or legs of the wearer. Further, the fastening components can also be easily disengaged from the mating fastening components to inspect the training pant for possible soiling. Thus, the training pant is configured to be pulled on or off over the hips of the wearer such as conventional training pants and can be readily applied or removed by disengaging the fastening components similar to conventional diapers. Moreover, the first and second fastening components can be repositioned if necessary after the training pant has been pulled on over the legs and hips of the wearer.

The interior corners are recessed relative to their inner end edges and inner side edges in order to minimize skin irritation. When the fastening system is engaged, a relatively high degree of separation force is concentrated near the leg openings of the absorbent article. This relatively high degree of separation force tends to cause the fastening components to separate from one another in a shear mode and/or peel mode near the inner end edges of the fastening components. By recessing the interior corners as disclosed in greater detail hereinafter, the likelihood of the fastening components coming into contact with the skin of the wearer are significantly reduced.

The degree to which the interior corners are recessed can be defined in terms of a boundary arc. The boundary arc represents a radius taken a fixed distance from two imaginary lines emanating from the inner side edge of the fastening component and from the longitudinally innermost point of the fastening component. For purposes of the present invention, the fixed distance is about 2 centimeters, particularly about 1.5 centimeters, such as exactly 1.5 centimeters, and more particularly about 1 centimeter, such as exactly 1 centimeter, for improved performance.

The refastenable seams are formed when the first and second fastening components are engaged with the mating fastening components. The refastenable seams are desirably relatively thin, narrow and flexible to afford the look and feel of a cloth garment. Thus, in particular embodiments, the refastenable seams have a length-to-width ratio of about 2 or greater, such as about 2 to about 25, particularly about 5 or greater, such as about 5 to about 8. The refastenable seams define a length dimension and a width dimension that is perpendicular to the length dimension. For a child of about 9 to about 15 kilograms (20–34 lbs.), for example, the length dimension is desirably from about 5 to about 13 centimeters, such as about 10 centimeters, and the width dimension is desirably from about 0.5 to about 3 centimeters, such as about 2 centimeters. Desirably although not necessarily, the length dimension is aligned generally parallel to the longitudinal axis of the absorbent article and the width dimension is aligned generally parallel to the transverse axis of the absorbent article. The term "generally parallel" as used herein refers to an angle within about 35 degrees or less of the referenced axis, and more particularly within about 20 degrees or less of the referenced axis.

The fastening components can comprise any refastenable fasteners suitable for absorbent articles, and desirably comprise mechanical fastening elements rather than adhesive fastening elements. Suitable mechanical fastening elements can be provided by interlocking geometric shaped materials, such as hooks, loops, bulbs, mushrooms, arrowheads, balls on stems, male and female mating components, buckles, snaps, or the like. In particular embodiments, the fastening components and mating fastening components comprise hook-and-loop fastening elements. One skilled in the art will recognize that the shape, density and polymer composition of the hooks and loops can be selected to obtain the desired level of securement between the fastening components and the mating fastening components. A more aggressive hook material can comprise a material with a greater average hook height, a greater percentage of directionally-aligned hooks, or a more aggressive hook shape.

As disclosed in copending U.S. patent application Ser. No. 60/112,709, filed on Dec. 18, 1998 by C. P. Olson et al. and titled "Absorbent Articles Having Differential Strength Refastenable Seam," the refastenable seam may include one or more main refastenable attachment zones and one or more enhanced refastenable attachment zones. The main and enhanced refastenable attachment zones may be constructed to provide differential levels of securement, and particularly augmented levels of securement at locations which are subject to greater levels of separation forces.

As disclosed in copending U.S. patent application Ser. No. 60/112,775, filed on Dec. 18, 1998 by C. P. Olson and titled "Absorbent Articles Having Hinged Fasteners," the refastenable seam may comprise individual fastening materials with narrow spacings therebetween. The narrow spacings provide a desirable hinge to improve fit and securement of the fastening components.

The disclosed absorbent articles are adapted to be worn adjacent to the body of a wearer to absorb and contain various exudates discharged from the body. The absorbent articles are desirably pre-fastened to provide a pant-like product for the user. The product can then be pulled on like a conventional training pant, and subsequently checked or removed with the ease of a diaper-like product. Moreover, the product may be applied like a diaper rather than like a pant. Supplemental releasable fastening means such as frangible point bonds may be employed to maintain the absorbent article in a pant configuration until the user intentionally disengages the fasteners.

The fastening system allows for easy inspection of the interior of the pant-like product. If necessary, the fastening system also allows the pant to be removed quickly and easily. This is particularly beneficial when the pant contains messy excrement. If desired, the caregiver can completely remove the pant-like product and replace it with a new one without having to remove the child's shoes and clothing. The present fastening system may be used with a wide variety of absorbent products, including training pants, diapers, incontinence garments, or other garments using mechanical or adhesive fasteners.

The present invention also pertains to a method of making an absorbent article, which is described in greater detail hereinafter. A more detailed description of the construction and design of one form of training pant can be found in U.S. Pat. No. 4,940,464 issued Jul. 10, 1990 to Van Gompel et al., which is incorporated herein by reference. The Van Gompel et al. patent describes various materials of which the training pant can be made, and a method of constructing a training pant.

Definitions

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on" and variations thereof are intended to mean that one element can be integral with another element, or that one element can be a separate structure bonded to or placed with or placed near another element.

"Elastic" and "elasticized" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric materials or composites be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven web" means a web of material which is formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

BRIEF DESCRIPTION OF THE DRAWINGS

The above-mentioned and other features of the present invention and the manner of attaining them will become more apparent, and the invention itself will be better understood by reference to the following description and the accompanying drawings, wherein similar features in different figures have been given the same reference numeral.

DETAILED DESCRIPTION OF THE DRAWINGS

The principles of the present invention can be incorporated into any suitable disposable absorbent article and its method of manufacture. Examples of such suitable articles include diapers, training pants, feminine hygiene products, incontinence products, other personal care or health care garments, or the like. For ease of explanation, the description hereafter will be in terms of a child's training pant.

Figure 1:
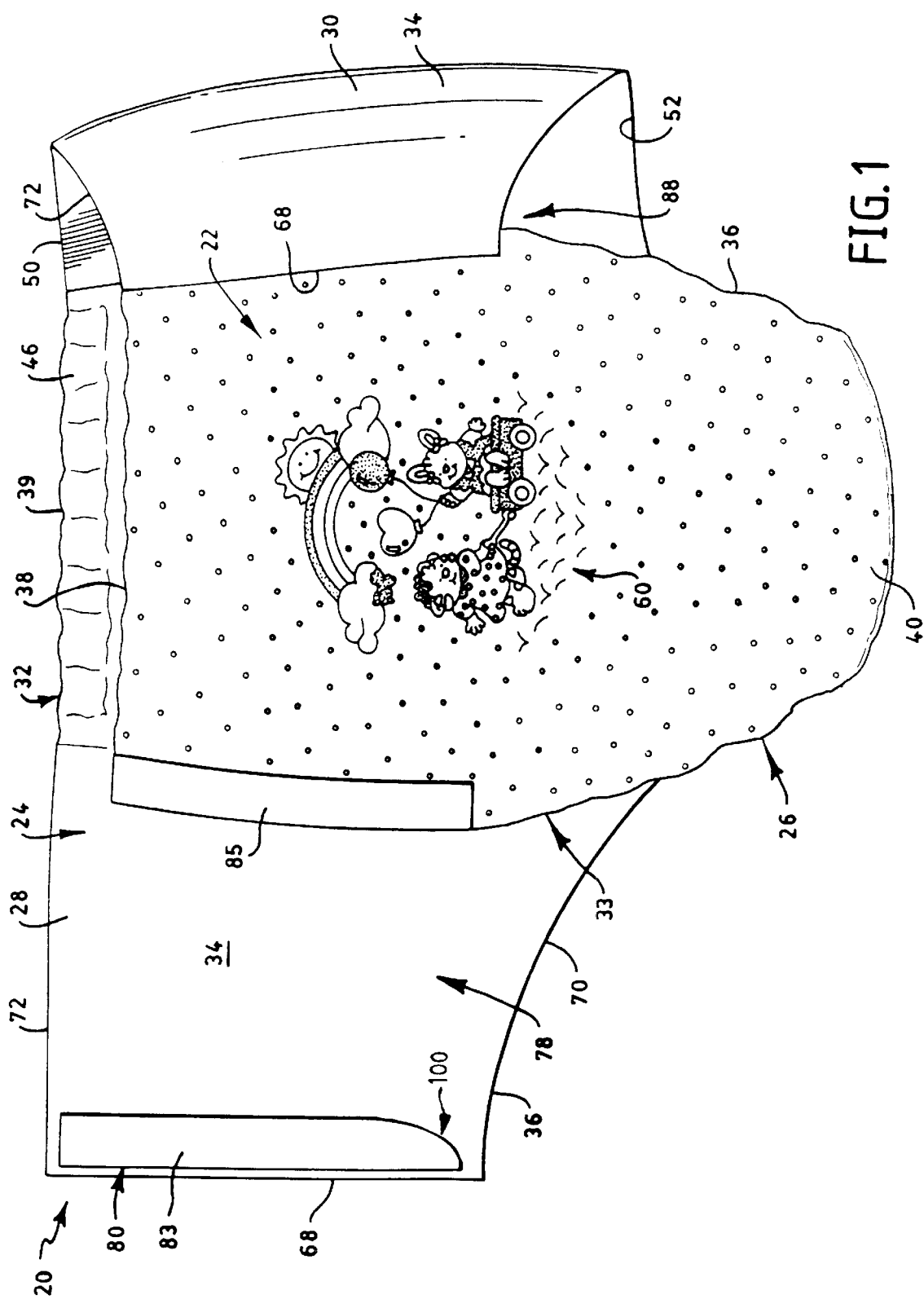
FIG. 1 illustrates a front perspective view of one type of disposable absorbent article incorporating the principles of the present invention, where the fastening system is shown engaged on one side of the absorbent article and disengaged on the other side of the absorbent article.

With reference to FIG. 1, a disposable absorbent article, such as a training pant 20, is illustrated in a partially fastened condition. The training pant 20 comprises an absorbent chassis 32 and a fastening system 80. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 2 and 3, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

Figure 2:
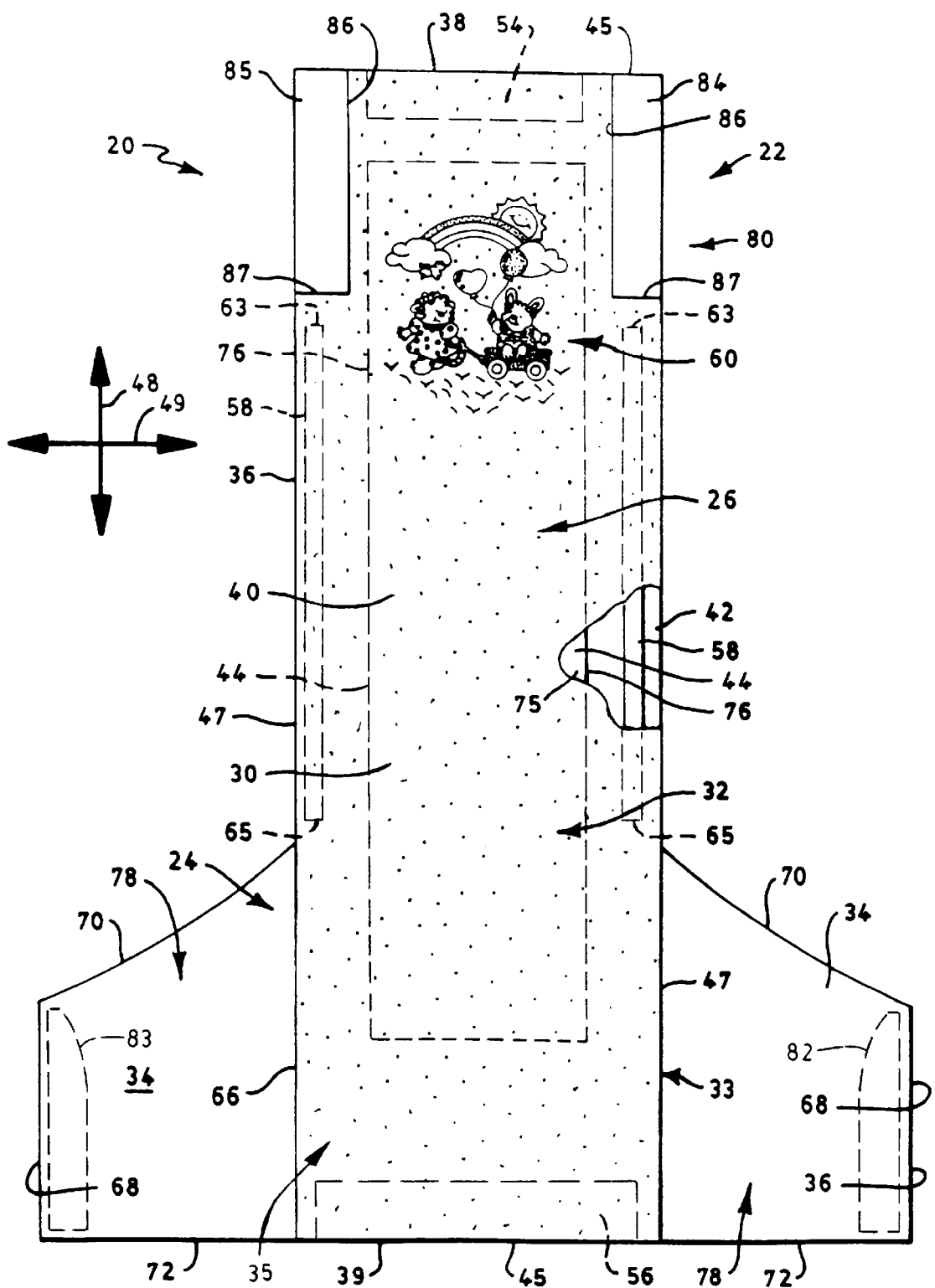
FIG. 2 illustrates a plan view of the disposable absorbent article shown in FIG. 1 in an unfastened, stretched and laid flat condition, and showing the surface of the article that faces away from the wearer, with portions cut away to show the underlying features.
Figure 3:
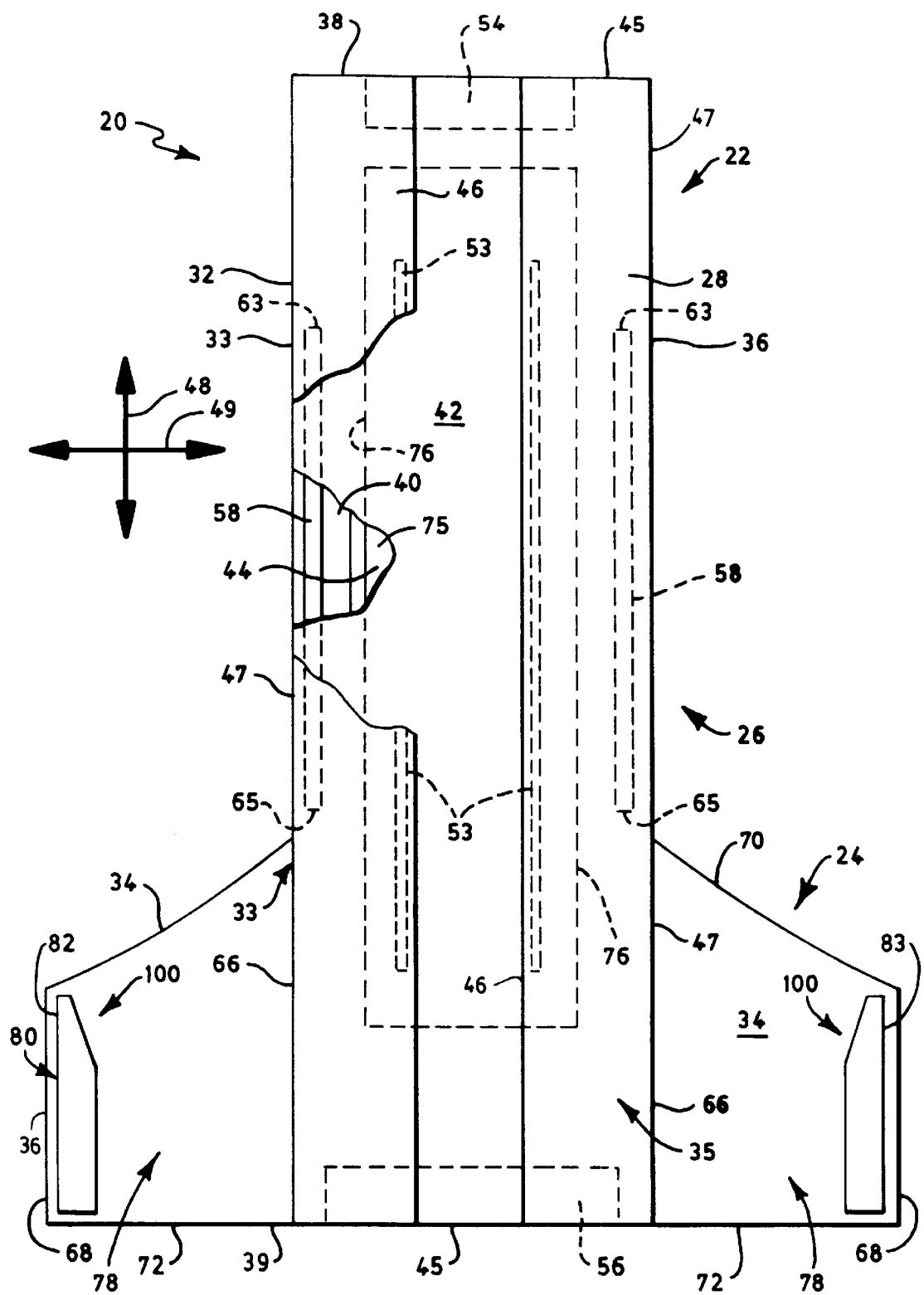
FIG. 3 illustrates a plan view similar to FIG. 2, but showing the surface of the article that faces the wearer when the article is worn, and with portions cut away to show the underlying features.

The illustrated absorbent chassis 32 comprises a rectangular composite structure 33 and a pair of transversely opposed side panels 34. The composite structure 33 and side panels 34 may be integrally formed or comprise two or more separate elements, as shown. The illustrated composite structure 33 comprises an outer cover 40, a bodyside liner 42 which is connected to the outer cover in a superposed relation, an absorbent assembly 44 (FIGS. 2 and 3) which is located between the outer cover and the bodyside liner, and a pair of containment flaps 46 (FIGS. 1 and 3). The rectangular composite structure 33 has opposite linear end edges 45 that form portions of the front and back waist edges 38 and 39, and opposite linear side edges 47 that form portions of the side edges 36 of the absorbent chassis 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as partially illustrated in FIG. 1, the front and back waist regions 22 and 24 are joined together to define a three dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer.

The crotch region 26 of the training pant 20 comprises the portion of the training pant which, when worn, is positioned between the legs of the wearer and covers the lower torso of the wearer. The side panels 34 comprise the portions of the training pant 20 which, when worn, are positioned on the side hip regions of the wearer. The back waist region 24 of the absorbent chassis 32 includes the transversely opposed side panels 34 and a center panel 35 (FIGS. 2 and 3) positioned between and connecting the side panels.

The waist edges 38 and 39 of the absorbent chassis 32 and the side panels 34 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 3) is operatively joined with each containment flap 46 in any suitable manner well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes a front waist elastic member 54, a rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges.

The leg elastic members 58 are desirably operatively joined to the outer cover 40 and/or bodyside liner 42 along the opposite side-edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members.

The flap elastic members 53, the waist elastics 54 and 56, and the leg elastics 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del., U.S.A.

The outer cover 40 desirably comprises a material that is substantially liquid impermeable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A. or from National Starch and Chemical Company, Bridgewater, N.J., U.S.A. The liquid permeable outer layer can be any suitable material and desirably one that provides a generally clothlike texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as liquid impermeable inner layer, or a single layer liquid impermeable outer cover 40, is a 1.0 mil polyethylene film commercially available from Edison Plastics Company of South Plainfield, N.J., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn., U.S.A.

As shown in FIGS. 1 and 2, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered outer cover graphic 60. In this design, the outer cover graphic 60 includes a rainbow, sun, clouds, wagon and balloon. Again, any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire bodyside liner 42 or may be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent assembly 44 (FIG. 3) is positioned between the outer cover 40 and the bodyside liner 42, which components can be joined together by any suitable means such as adhesives as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or may be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A. and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and comprises a blend of wood pulp fluff and superabsorbent material. One preferred type of fluff is identified with the trade designation CR1654, available from Kimberly-Clark Corporation, Neenah, Wis., U.S.A. and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that maintains the integrity and/or shape of absorbent assembly.

The absorbent chassis 32 can also incorporate other materials that are designed primarily to receive, temporarily store, and/or transport liquid along the mutually facing surface with absorbent assembly 44, thereby maximizing the absorbent capacity of absorbent assembly. One suitable material is referred to as a surge layer (not shown) and comprises a material having a basis weight of about 50 grams per square meter, and comprising a through-air-bonded-carded web of a homogenous blend of 60 percent 3 denier bicomponent fiber comprising a polyester core/polyethylene sheath, commercially available from BASF Corporation, and 40 percent 6 denier polyester fiber, commercially available from Hoechst Celanese Corporation, Portsmouth, Va. U.S.A.

The absorbent assembly 44 is considered to have an absorbent batt 75 that represents the primary absorbent structure of the absorbent assembly. The absorbent batt 75 includes opposite side edges 76 that are generally longitudinally oriented within the absorbent chassis 32 (FIGS. 2 and 3).

As noted previously, the illustrated training pant 20 has a side panel 34 disposed on each side of the absorbent chassis 32. The pair of transversely opposed side panels 34 can be permanently bonded to the composite structure 33 of the absorbent chassis 32 in at least one of the waist regions 22 and 24 and releasably attached to the absorbent chassis in the opposite waist region. For example, as shown best in FIGS. 2 and 3, the side panels 34 can be permanently bonded to and extend transversely beyond the side edges 36 of the absorbent chassis 32 in the back waist region 24 along an attachment line 66.

The illustrated side panels 34 define a distal edge 68 that is spaced from the attachment line 66, a leg end edge 70, and a waist end edge 72. The leg end edge 70 and waist end edge 72 extend from the side edges 47 of the composite structure 33 to the distal edges 68. The leg end edges 70 of the side panels 34 form part of the side edges 36 of the absorbent chassis 32 and are desirably although not necessarily angled relative to the transverse axis 49 to provide greater coverage toward the back of the pant as compared to the front of the pant. The waist end edges 72 are desirably parallel to the transverse axis 49 and form part of the back waist edge 39 of the absorbent chassis 32.

In particular embodiments for improved fit and appearance, the side panels 34 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 desirably have an average length dimension of about 10 centimeters or greater, such as about 15 centimeters. As illustrated the side panels 34 extend from the waist opening 50 to one of the leg openings 52 and have a continually decreasing length dimension moving from the attachment line 66 to the distal edge 68.

The side panels 34 can be permanently bonded to the absorbent chassis 32 along the attachment line 66 using attachment means known to those skilled in the art such as adhesive, thermal or ultrasonic bonding. In such a configuration, each of the side panels 34 can be releasably attached to the absorbent chassis 32 in the front waist region 22 of the training pant 20 as will be discussed hereinafter in more detail. Alternatively, the side panels 34 can be permanently bonded to the side edges 36 in the front waist region 22 and releasably attached to the side edges 36 in the back waist region 24 if it is desired that the fasteners be located towards the back of the wearer. Such a configuration may be desirable to prevent a wearer from unfastening the article prematurely. The side panels can also be formed as a portion of a component of the composite structure 33, such as the outer cover or bodyside liner.

Each of the side panels 34 can include one or more individual, distinct pieces of material. In particular embodiments, for example, each side panel 34 can include front and back side panel portions that are joined at a seam (not shown). Still alternatively, each individual side panel 34 can include a single piece of material which is folded over upon itself along an intermediate fold line (not shown).

The side panels 34 desirably comprise an elastic material capable of stretching in a direction parallel to the transverse axis 49 of the training pant 20. In particular embodiments, each side panel 34 can comprise an interior portion 78 disposed between the distal edge 68 and the center panel 35 of the back waist region 24. In the illustrated embodiment, the interior portion 78 is disposed between the distal edge 68 and the side edges 47 of the rectangular composite structure 33. The elastic material of the side panels 34 can be disposed in the interior portions 78 to render the side panels elastomeric in a direction parallel to the transverse axis 49. Most desirably, each side panel 34 is elastomeric in a direction parallel to the transverse axis 49 from the waist end edge 72 to the leg end edge 70.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Mormon; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42.

The training pant 20 according to the present invention also includes a fastening system 80 for securing the training pant about the waist of the wearer (FIGS. 2 and 3). The illustrated fastening system 80 includes first and second fastening components 82 and 83 that are adapted to refastenably connect to first and second mating fastening components 84 and 85. In one embodiment, one surface of each of the first and second fastening components 82 and 83 comprises a plurality of engaging elements that project from that surface. The engaging elements of these fastening components 82 and 83 are adapted to repeatedly engage and disengage the engaging elements of the mating fastening components 84 and 85.

In one particular embodiment, the first and second fastening components 82 and 83 each comprise hook type fasteners and the first and second mating fastening components 84 and 85 each comprise complementary loop type fasteners. Loop type fasteners typically comprise a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically comprise a fabric or material having a base or backing structure and a plurality of hook members extending upwardly from at least one surface of the backing structure. In contrast to the loop type fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the first fastening components 82 and 83 for example are available from Velcro Industries B.V., Amsterdam, Netherlands or affiliates thereof, and are identified as Velcro HTH-829 with a unidirectional hook pattern and having a thickness of about 0.089 millimeters (3.5 mils) and HTH-851 with a unidirectional hook pattern and having a thickness of about 0.051 millimeters (2 mils).

With reference to FIG. 3, the first and second fastening components 82 and 83 are desirably located on the inner surface 28 of the training pant 20 in the back waist region 24. The first and second fastening components 82 and 83 are desirably positioned along the distal edge 68 of the side panels 34. The first and second fastening components 82 and 83 can be adhered to the side panels 34 by any means known to those skilled in the art such as adhesive bonds, sonic bonds or thermal bonds.

With reference to FIG. 2, the first and second mating fastening components 84 and 85 can be located on the outer surface 30 of the training pant 20 in the front waist region 22. The first and second mating fastening components 84 and 85 are sized to receive the first and second fastening components 82 and 83 and are desirably positioned along the side edges 36 of the absorbent chassis 32, and in particular along the linear side edges 47 of the rectangular composite structure 33, abutting the front waist edge 38. In particular embodiments, the mating fastening components 84 and 85 have their inner side edges 86 disposed transversely outward from and closely adjacent to the side edges 76 of the absorbent batt 75. Moreover, the leg elastic members 58 are desirably axially aligned with the mating fastening components 84 and 85. The front terminal points 63 of the leg elastic members 58 are desirably located adjacent inner end edges 87 of the respective mating fastening components 84 and 85, and the back terminal points 65 of the leg elastic members are desirably located adjacent the longitudinally innermost parts of the side panels 34.

Figure 4:
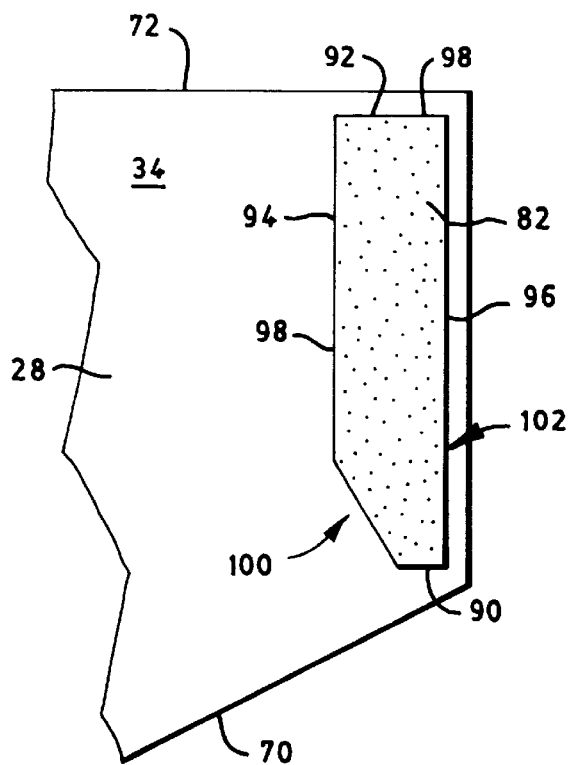
FIG. 4 illustrates an enlarged plan view of a side panel of the absorbent article shown in FIGS. 1–3, in an unfastened, stretched and laid flat condition and showing the surface of the article that faces the wearer when the article is worn.

An enlarged view of the inner surface 28 of one side panel 34, including one of the two fastening components 82 and 83 is shown in FIG. 4. Each fastening component 82 and 83 defines an inner end edge 90, an outer end edge 92 located longitudinally opposite the inner end edge, an inner side edge 94, and an outer side edge 96 located transversely opposite the outer side edge. Each inner end edge 90 is disposed toward the leg end edge 70 of its corresponding side panel 34, toward the transverse centerline of the training pant, and, when the fastening components are engaged, toward the adjacent leg opening 52. Each outer end edge 92 is disposed toward the waist end edge 72 of its corresponding side panel 34, toward the back waist edge 39 of the absorbent chassis 32, and, when the fastening components are engaged, toward the waist opening 50. The inner side edges 94 are disposed toward one another and also toward the longitudinal centerline of the training pant 20. Each outer side edge 96 is disposed toward the distal edge 68 of its corresponding side panel 34. The edges 90, 92, 94 and 96 of each fastening component 82 and 83 can be linear or curved and jointly define a peripheral edge 98 of the fastening component.

Each first and second fastening component 82 and 83 has an interior corner 100 that corresponds generally to the corner of the fastening component 82 or 83 that is disposed toward the longitudinal and transverse center of the training pant 20. According to the present invention, the interior corner 100 is recessed relative to inner end edge 90 and the inner side edge 94. When the fastening system is engaged, a relatively high degree of separation force is concentrated near the leg openings 52. This relatively high degree of separation force tends to cause the fastening components to separate from one another in a shear mode and/or peel mode near the inner end edge 90 of the fastening components 82 and 83. By recessing the interior corner 100 to a significant degree, the likelihood of the fastening components 82 and 83 coming into contact with the skin of the wearer is significantly reduced.

Figure 5:
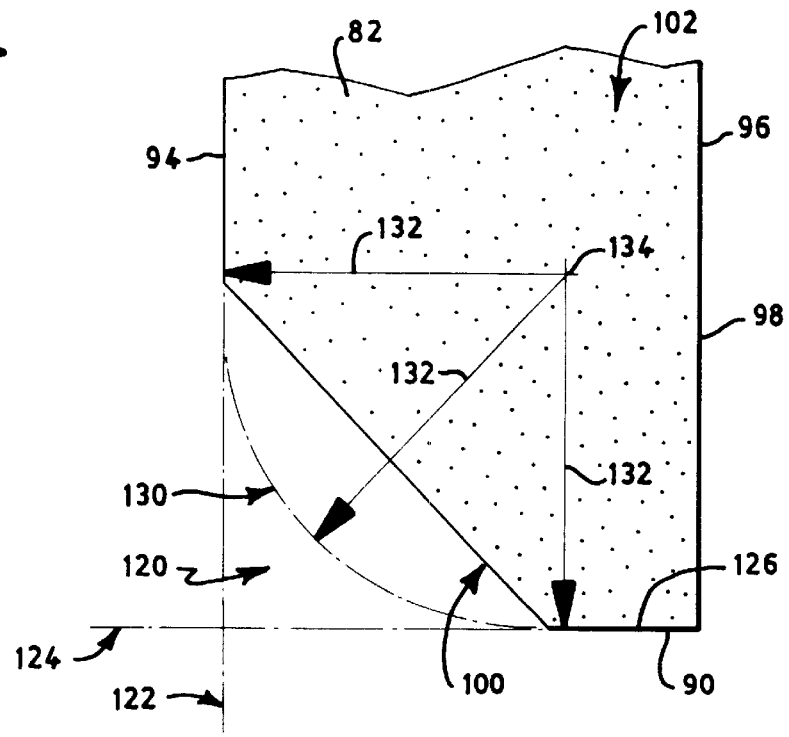
FIG. 5 illustrates an enlarged view of an inner portion of a fastening component shown in FIG. 4.

The meaning of the interior corner 100 being recessed relative to the inner end edge 90 and inner side edge 94 can best be understood with reference to FIG. 5, which shows an inner portion 102 of the first fastening component 82 enlarged, stippled, and in isolation. The interior corner 100 of the fastening component 82 is recessed or displaced from a region 120 that is formed inside a first imaginary line 122 and a second imaginary line 124. The first imaginary line 122 continues longitudinally inward from the inner side edge 94. The second imaginary line 124 is perpendicular to the first imaginary line 122 and intersects a point 126 on the peripheral edge 98 that the longitudinally innermost point of the fastening component 82. In the illustrated embodiment, the inner end edge 90 is perpendicular to the longitudinal axis 48 of the training pant 20 and thus the longitudinally innermost point 126 is located at any point along the transverse segment of the inner end edge.

The degree to which the interior corner 100 is recessed from the region 120 created within the imaginary lines 122 and 124 can be defined in terms of a boundary arc 130. The boundary arc 130 represents a radius taken a fixed distance from the imaginary lines 122 and 124. The fixed distance is illustrated in FIG. 5 by rays 132 emanating from a central point 134. For purposes of the present invention, the fixed distance is about 2 centimeters, particularly about 1.5 centimeters, such as exactly 1.5 centimeters, and more particularly about 1 centimeter, such as exactly 1 centimeter, for improved performance. Thus, the peripheral edges 98 of the fastening components 82 and 83 at their interior corners 100 suitably lie within the boundary arc 130 defined by a radius of about 2 centimeters applied to a first imaginary line 122 projecting from the inner side edge and a perpendicular secondary imaginary line 124 projecting from the longitudinally innermost point 126 of the fastening component.

Figure 6:
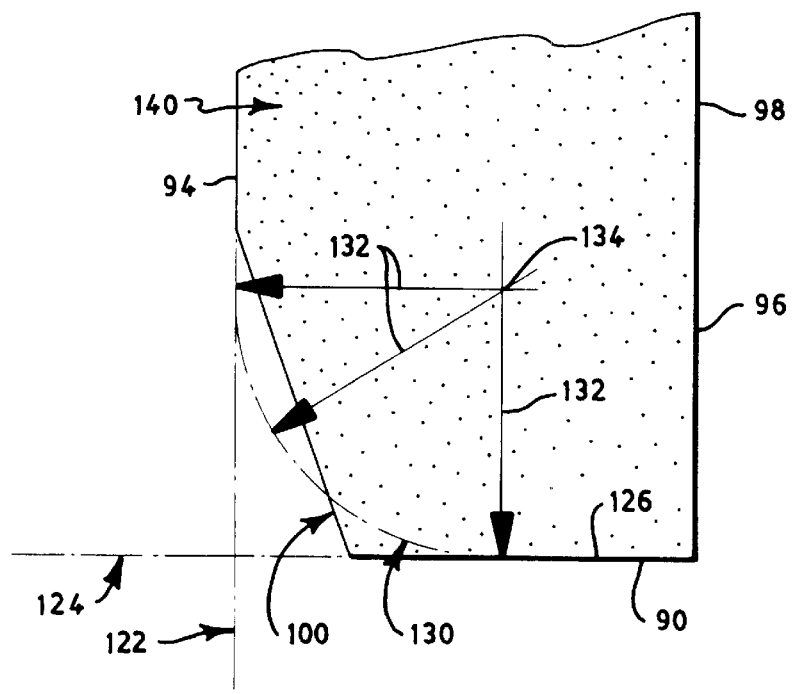
FIG. 6 illustrates a comparative fastening component.

It can be seen from FIG. 5 that the peripheral edge 98 of the first fastening component 82 at the interior corner 100 lies inside the boundary arc 130. For purpose of illustration and comparison, a fastening component 140 is shown in FIG. 6 with the plotted imaginary lines 122 and 124, boundary arc 130, rays 132 and central point 134 as described above. The peripheral edge 98 of this fastening component 140 at the interior corner 100 substantially crosses the boundary arc 130 and thus does not lie inside the boundary arc.

Figures 7A, 7B, 7C:
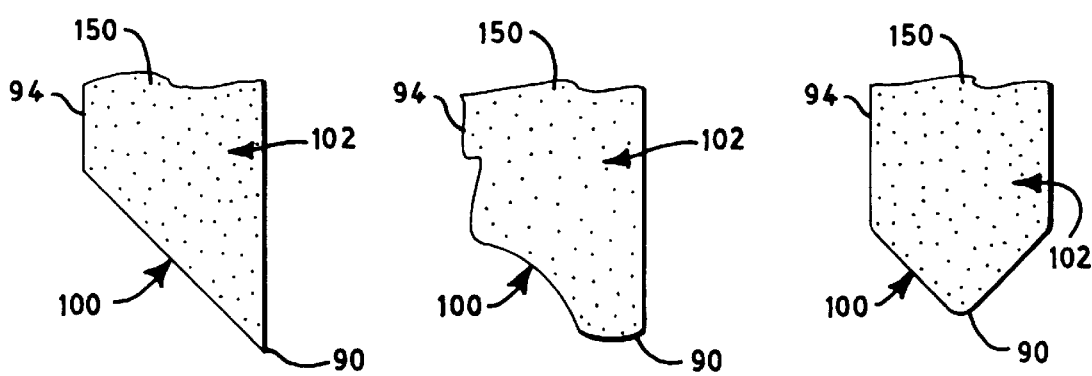
FIGS. 7A, 7B and 7C illustrate various fastening components having recessed interior edges according to particular embodiments of the present invention.

The fact that the interior corner 100 is recessed relative to inner end edge 90 and the inner side edge 94 does not significantly inhibit the variety of shapes that the peripheral edge 98 may take at the interior corner. FIGS. 7A through 7C illustrate several alternative fastening components 150 having a recessed interior corner 100. With respect to FIG. 7B, it should be pointed out that the inner side edge 94 of the fastening component 150 has a scalloped edge and that the first imaginary line 122 would be taken from the line formed between the transversely innermost portions of the scalloped edge. It is noted with respect to FIG. 7C that other corners besides the interior corner 100 may be recessed, and in one particular embodiment the fastening component 150 includes four corners and all are recessed. In particular embodiments, all corners can be recessed somewhat with the interior corner 100 being recessed to a greater extent than the other corners.

The fastening components 82 and 150 illustrated in FIGS. 5 and 7 have interior corners 100 directed toward the bottom left-hand side of the figures. Fastening components for use on the opposite side of the training pant 20 can comprise mirror images of the illustrated fastening components 82 and 150.

With reference to FIG. 2, the first and second mating fastening components 84 and 85 can be located on the outer surface 30 of the training pant 20 in the front waist region 22. The first and second mating fastening components 84 and 85 are sized to receive the first and second fastening components 82 and 83 and are desirably positioned along the side edges 36 of the absorbent chassis 32, and in particular along the linear side edges 47 of the rectangular composite structure 33, abutting the front waist edge 38. In particular embodiments, the mating fastening components 84 and 85 can have their inner side edges 86 disposed transversely outward from and closely adjacent to the side edges 76 of the absorbent batt 75. Moreover, the leg elastic members 58 are desirably axially aligned with the mating fastening components 84 and 85. The front terminal points 63 of the leg elastic members 58 are desirably located adjacent inner end edges 87 of the respective mating fastening components 84 and 85, and the back terminal points 65 of the leg elastic members are desirably located adjacent the longitudinally innermost parts of the side panels 34.

In particular embodiments, the fastening components 82 and 83 can be spaced inward from the distal edge 68 and the end edges 70 and 72 in order to protect the wearer from irritation that might be caused by contact with the fastening component. Specifically, the fastening components 82 and 83 can be spaced transversely inward from the distal edge 68 by about 1 to about 15 millimeters, particularly about 1 to about 5 millimeters, such as about 2 millimeters. Also, the fastening components 82 and 83 can be spaced longitudinally inward from the leg end edge 70 and from the waist end edge 72 by about 2 millimeters or more, particularly about 5 millimeters or more, such as from about 5 to about 15 millimeters. Similarly, in the front waist region 22 the mating fastening components 84 and 85 are desirably spaced transversely inward from the side edge 36 by about 1 to about 50 millimeters, particularly about 1 to about 10 millimeters, such as about 2 millimeters, and are longitudinally spaced inward from the end edge 45 by about 2 millimeters or more, particularly about 5 millimeters or more, such as from about 5 to about 15 millimeters. The degree of spacing balances the fact that a smaller distance is harder for children and parents to remove but provides a more garment-like appearance, while a larger distance is easier for children and parents to remove but provides a loose and floppy appearance that is not garment-like.

The first and second mating fastening components 84 and 85 can be adhered to the outer cover 40 by any means known to those skilled in the art such as adhesive bonds, sonic bonds or thermal bonds. In an alternative embodiment, the training pant 20 includes only a single mating fastening component disposed in the front waist region 22 for refastenably connecting to the first and second fastening components 82 and 83 (not shown). In a further alternative embodiment, the outer cover 40 functions as a mating fastening component in that it comprises a material that is releasably engagable with the first and second fastening components 82 and 83. The first and second mating fastening components 84 and 85 are desirably rectangular, although they may alternatively be square, round, oval, curved or otherwise nonrectangularly shaped.

When the fastening components and the mating fastening components 82–85 are releasably engaged, the side edges 36 of the absorbent chassis 32 in the crotch region 26 define the leg openings 52, and the waist edges 38 and 39 of the absorbent chassis, including the waist end edges 72 of the side panels define the waist opening 50. Due to the composite structure 33 being rectangular and the side panels 34 being attached in the back waist region 24, the side edges 36 of the absorbent chassis 32 in the front waist region 22 and the crotch region 26 are aligned with one another and are parallel to the longitudinal axis 48, that is, they form common linear edges.

When connected, the fastening components and the mating fastening components 82–85 form a refastenable seam 88 (FIG. 1). In particular embodiments, each of the fastening components and the mating fastening components 82–85 defines a length dimension aligned generally parallel with the longitudinal axis 48 of the training pant 20 and a width dimension aligned generally parallel with the transverse axis 49 of the training pant. For a child of about 9 to about 15 kilograms (20–30 pounds), for example, the length dimension of the fastening components and mating fastening components is desirably from about 5 to about 13 centimeters, such as about 10 centimeters, and the width dimension is desirably from about 0.5 to about 3 centimeters, such as about 1 centimeter. The fastening components and the mating fastening components desirably have a length-to-width ratio of about 2 or greater, such as about 2 to about 25, and particularly about 5 or greater, such as about 5 to about 8.

The absorbent chassis 32 and the fastening system 80 together define a refastenable pant having a waist opening 50 and a pair of leg openings 52. When the fastening system is engaged, it can be appreciated that the refastenable pant includes a pair of refastenable seams 88 extending from the waist opening to each leg opening, a pair of elastomeric side panels 34 extending from the waist opening to each leg opening, an elastomeric front waistband 54 disposed in the front waist region and positioned between the pair of refastenable seams, an elastomeric back waistband 56 disposed in the back waist region and positioned between the pair of elastomeric side panels, and a pair of elastomeric leg members 58 which partially encircle each leg opening. Each elastomeric leg member 58 extends from adjacent a refastenable seam 88 in the front waist region 22 to adjacent an elastomeric side panel 34 in the back waist region 24.

The training pant 20 may further include releasable side bonds (not shown) for improved reliability of maintaining the pant in a prefastened condition particularly when it is being pulled on or off over the hips of the wearer. Such releasable side bonds are desirably configured to be readily broken such that the caregiver can easily remove the training pant 20 after it has been soiled. The releasable side bonds desirably comprise ultrasonic point bonds. Absorbent articles including such releasable side bonds are further described in U.S. patent application Ser. No. 09/100,574 titled "Disposable Absorbent Articles Having Passive Side Bonds And Adjustable Fastening Systems" filed Jun. 19, 1998 by Elsberg, which is incorporated herein by reference.

Figure 8:
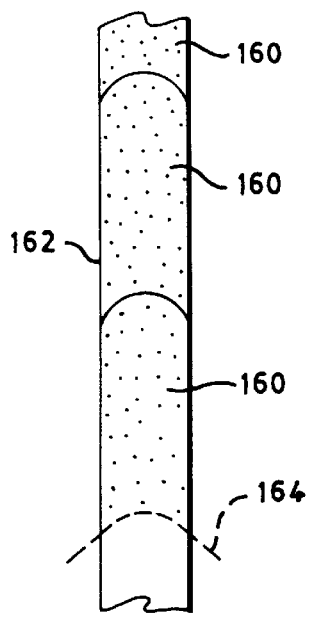
FIG. 8 illustrates a method of making individual fastening component segments for use in making the absorbent article.
Figure 9:
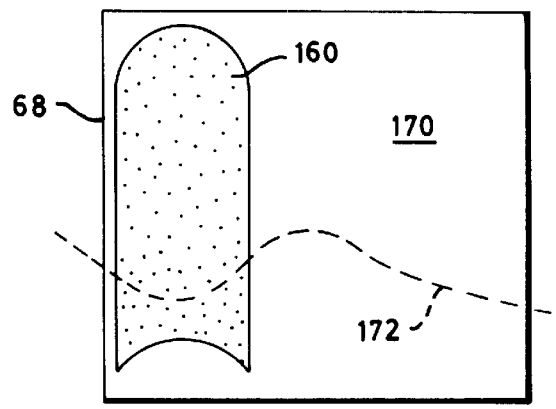
FIG. 9 illustrates attachment of the individual fastening component segments of FIG. 8 to a section of side panel material.
Figure 10:
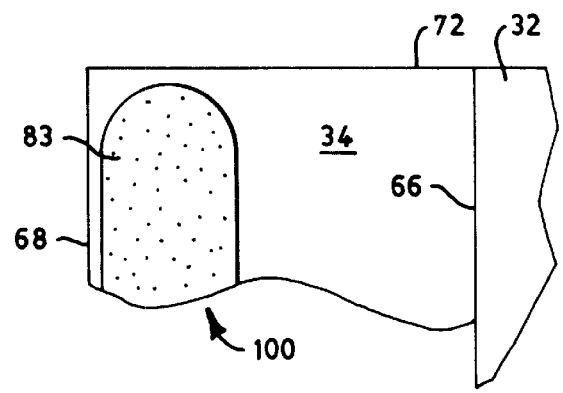
FIG. 10 illustrates a side panel of an absorbent article formed using the materials shown in FIG. 9.

The methods of the different aspects of the present invention are directed at reliably and consistently providing the refastenable training pant 20 as described herein and representatively illustrated in the Figures. The various components of the training pant 20 are integrally assembled together employing various types of suitable attachment means, such as adhesive, sonic and thermal bonds or combinations thereof. One particularly beneficial method of manufacturing portions of training pant 20 is illustrated in FIGS. 8–10. Individual fastening component segments 160 are die cut from a strip 162 of fastening component material.

The die cut line 164 used to cut the strip 162 into individual segments 160 is desirably a curved shape, and particularly a curved shape having a radius of about 1 centimeter or greater.

The resulting individual segments 160 are then bonded to a section 170 of side panel material, preferably adjacent an edge that will become the distal edge 68 of a side panel 34 in the training pant 20 (FIG. 9). The individual segment 160 and the side panel section 170 are then jointly die cut to form a side panel composite structure consisting of a side panel 34 with a fastening component 82–85 bonded thereto. The die cut line 172 for this operation is desirably a curved shape having a radius of about 1 centimeter or greater.

With reference to FIG. 10, the side panel composite structure can then be bonded to other components of the absorbent chassis 32 at an attachment line 66 to form a side panel 34 including a fastening component 83 having a recessed interior corner 100.

Figure 11A:
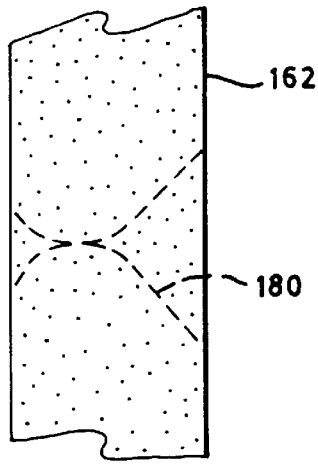
FIGS. 11A and 11B illustrate a method of directly making individual fastening components from a strip of fastening component material.
Figure 11B:
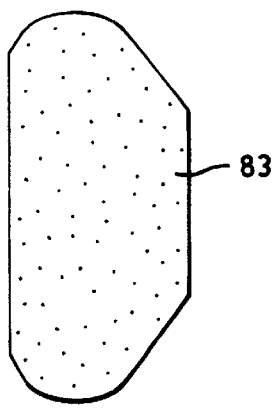

In an alternative embodiment, a strip 162 of fastening component material may be die cut directly into individual fastening components 83 having a recessed interior corner 100. One suitable die cut line 180 is the multiple component die cut line illustrated in FIG. 11.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An absorbent article, comprising:
    an absorbent chassis defining a longitudinal axis, a transverse axis, inner and outer surfaces, opposite first and second waist regions, and a crotch region which extends between and interconnects the first and second waist regions; and
    a fastening system comprising first and second fastening components disposed in the first waist region and adapted to releasably engage at least one mating fastening component disposed in the second waist region, each first and second fastening component defining at least four corners, one of the corners being an interior corner disposed toward the longitudinal and transverse center of the absorbent chassis, the interior corner being recessed to a greater extent than the other of the at least four corners.

2. The absorbent article of claim 1, wherein each first and second fastening component has a length dimension, a width dimension, and a length-to-width ratio of about 2 or greater.

3. The absorbent article of claim 2, wherein each first and second fastening component has a length-to-width ratio of about 5 or greater.

4. The absorbent article of claim 2, wherein the length dimension is aligned generally parallel to the longitudinal axis.

5. The absorbent article of claim 1, further comprising first and second mating fastening components disposed in the second waist region adjacent opposite side edges of the absorbent chassis.

6. The absorbent article of claim 5, wherein each first and second mating fastening component has a length dimension aligned generally parallel to the longitudinal axis, a width dimension, and a length-to-width ratio of about 2 or greater.

7. The absorbent article of claim 1, wherein the first and second fastening components are attached to respective first and second elastomeric side panels.

8. The absorbent article of claim 1, wherein each fastening component defines an inner end edge, an outer end edge located longitudinally opposite the inner end edge, an inner side edge, and an outer side edge located transversely opposite the inner side edge, each inner end edge being disposed toward the transverse centerline of the absorbent chassis and each inner side edge being disposed toward the longitudinal centerline of the absorbent chassis, and the interior corner is recessed relative to the inner end edge and the inner side edge.

9. The absorbent article of claim 1, wherein the first and second fastening components are disposed on the inner surface of the absorbent article.

10. An absorbent article, comprising:
   an absorbent chassis defining a longitudinal axis, a transverse axis, inner and outer surfaces, opposite first and second waist regions, and a crotch region which extends between and interconnects the first and second waist regions; and
   a fastening system comprising first and second fastening components disposed on the inner surface in the first waist region and adapted to releasably engage at least one mating fastening component disposed in the second waist region, each first and second fastening component defining an interior corner disposed toward the longitudinal and transverse center of the absorbent chassis, wherein each interior corner has a peripheral edge that lies within a boundary arc defiled by a radius of about 1 centimeter applied to a first imaginary line projecting from an inner side edge of each fastening component and a perpendicular secondary imaginary line projecting from a longitudinally innermost point of each fastening component.

11. The absorbent article of claim 10, wherein each interior corner has a peripheral edge that lies within a boundary arc defined by a radius of about 2 centimeters applied to a first imaginary line projecting from an inner side edge of each fastening component and a perpendicular secondary imaginary line projecting from a longitudinally innermost point of each fastening component.

12. The absorbent article of claim 10, wherein each interior corner has a peripheral edge that lies within a boundary arc defined by a radius of about 1.5 centimeters applied to a first imaginary line projecting from an inner side edge of each fastening component and a perpendicular secondary imaginary line projecting from a longitudinally innermost point of each fastening component.

13. An absorbent article, comprising:
   an absorbent chassis defining a longitudinal axis, a transverse axis, inner and outer surfaces, opposite front and back waist regions, a crotch region which extends between and interconnects the front and back waist regions, and transversely opposed elastomeric side panels disposed in the back waist region; and
   a fastening system comprising first and second fastening components disposed in the back waist region and adapted to releasably engage at least one mating fastening component disposed in the front waist region, the fastening components comprising refastenable mechanical fastening elements, each first and second fastening component defining at least four corners, one of the corners being an interior corner disposed toward the longitudinal and transverse center of the absorbent chassis, the interior corner being recessed to a greater extent than the other of the at least four corners.

14. The absorbent article of claim 13, wherein the mechanical fastening elements comprise interlocking geometric shaped materials.

15. The absorbent article of claim 13, wherein the first and second fastening components are disposed on the inner surface of the absorbent article.

16. A method of making an absorbent article, comprising:
   forming an absorbent chassis defining a longitudinal axis, a transverse axis, opposite first and second waist regions, and a crotch region which extends between and interconnects the first and second waist regions;
   incorporating first and second fastening components in the absorbent chassis in the first waist region, each first and second fastening component defining an interior corner disposed toward the longitudinal and transverse center of the absorbent chassis, the interior corner being recessed, wherein incorporating the first and second fastening components comprises:
   providing a strip of fastening component material;
   die cutting the strip into individual segments;
   bonding individual segments to a side panel section of the absorbent chassis; and
   jointly die cutting the individual segments and the side panel section, wherein the die cut line is curved and has a radius of about 1 centimeter or greater; and
   incorporating at least one mating fastening component in the absorbent chassis in the second waist region, the fastening components adapted to releasably engage the mating fastening component.

17. A method of making an absorbent article, comprising:
   forming an absorbent chassis defining a longitudinal axis, a transverse axis, opposite first and second waist regions, and a crotch region which extends between and interconnects the first and second waist regions;
   incorporating first and second fastening components in the absorbent chassis in the first waist region, each first and second fastening component defining an interior corner disposed toward the longitudinal and transverse center of the absorbent chassis, the interior corner being recessed, wherein incorporating the first and second fastening components comprises:
   providing a strip of fastening component material; and
   die cutting the strip into individual fastening components each having a recessed corner with a radius of about 1 centimeter or greater; and
   incorporating at least one mating fastening component in the absorbent chassis in the second waist region, the fastening components adapted to releasably engage the mating fastening component.

18. An absorbent article, comprising:
   an absorbent chassis defining a longitudinal axis, a transverse axis, inner and outer surfaces, opposite first and second waist regions, and a crotch region which extends between and interconnects the first and second waist regions; and
   a fastening system comprising first and second fastening components disposed on the inner surface in the first waist region and adapted to releasably engage at least one mating fastening component disposed in the second waist region, each first and second fastening component defining at least four corners, one of the corners being an interior corner disposed toward the longitudinal and transverse center of the absorbent chassis, the interior corner being recessed to a greater extent than at least one of the other of the at least four corners.

19. The absorbent article of claim 18, wherein the interior corner is recessed to a greater extent than at least two of the other of the at least four corners.

20. A method of making an absorbent article, comprising:

forming an absorbent chassis defining a longitudinal axis, a transverse axis, opposite first and second waist regions, and a crotch region which extends between and interconnects the first and second waist regions;

incorporating first and second fastening components in the absorbent chassis in the first waist region, each first and second fastening component defining an interior corner disposed toward the longitudinal and transverse center of the absorbent chassis, the interior corner being recessed, wherein incorporating the first and second fastening components comprises:

providing a strip of fastening component material;

die cutting the strip into individual segments;

bonding individual segments to a side panel section of the absorbent chassis; and jointly die cutting the individual segments and the side panel section; and incorporating at least one mating fastening component in the absorbent chassis in the second waist region, the fastening components adapted to releasably engage the mating fastening component.

* * * * *